United States Patent

Urso

[11] Patent Number: 5,816,271
[45] Date of Patent: Oct. 6, 1998

[54] SELF-GUIDING FLOSSER

[75] Inventor: Charles L. Urso, Waltham, Mass.

[73] Assignee: Dynaproducts, Inc., Nashua, N.H.

[21] Appl. No.: 572,051

[22] Filed: Dec. 14, 1995

[51] Int. Cl.⁶ .................................................. A61C 15/04
[52] U.S. Cl. ........................ 132/322; 132/325; 132/326
[58] Field of Search .................................. 132/325, 326, 132/322, 323, 324, 327

[56] References Cited

U.S. PATENT DOCUMENTS

| | | | |
|---|---|---|---|
| 1,110,680 | 9/1914 | Gamble | 132/325 |
| 1,171,177 | 2/1916 | De L'eau | 132/324 |
| 1,279,026 | 9/1918 | Sievers | 132/324 |
| 2,443,415 | 6/1948 | Buscarino | 132/323 |
| 2,784,722 | 3/1957 | Chamberlin et al. | 132/324 |
| 3,106,216 | 10/1963 | Kirby | 132/326 |
| 3,421,524 | 1/1969 | Waters | 132/92 |
| 3,667,483 | 6/1972 | McCabe . | |
| 3,759,274 | 9/1973 | Warner | 132/322 |
| 3,799,177 | 3/1974 | Bragg | 132/92 |
| 3,847,167 | 11/1974 | Brien . | |
| 4,094,328 | 6/1978 | Ray | 132/325 |
| 4,245,658 | 1/1981 | Lecouturier . | |
| 4,326,549 | 4/1982 | Hinding . | |
| 4,458,702 | 7/1984 | Grollimund . | |
| 4,586,521 | 5/1986 | Urso . | |
| 4,706,695 | 11/1987 | Urso . | |
| 5,016,660 | 5/1991 | Boggs | 132/322 |
| 5,069,233 | 12/1991 | Ritter . | |
| 5,085,236 | 2/1992 | Odneal et al. . | |
| 5,176,157 | 1/1993 | Mazza | 132/325 |
| 5,188,133 | 2/1993 | Romanus | 132/322 |
| 5,323,796 | 6/1994 | Urso | 132/322 |
| 5,647,385 | 7/1997 | Zebuhr . | |

FOREIGN PATENT DOCUMENTS

| | | | |
|---|---|---|---|
| 3920256 | 2/1990 | Germany | 132/323 |
| 9011057 | 10/1990 | WIPO | 132/325 |

*Primary Examiner*—Todd E. Manahan
*Assistant Examiner*—Eduardo C. Robert
*Attorney, Agent, or Firm*—Brooks & Kushman P.C.

[57] ABSTRACT

A flosser includes a frame (2) having a pair of tines (42) mounted on it for supporting a span of floss (62). At least one of pair the tines is pivotally supported for moving toward and away from the other of the pair of tines. Gear-driven capstans (24, 26) are provided for reciprocating the span of floss longitudinally between the tines, while a cam (9) and cam follower (11) act on a lever (32) for reciprocating the tines vertically. A spring (48) urges the tines to move laterally apart to an open position. Each of a pair of engaged sector gears (46) is fixed to a respective tine so that lateral movement of the tines is symmetrical. The spring is adjustable so that when the moving floss span encounters tooth resistance, floss tension increases to overcome the spring force and move the tines toward a closed position. The bulbs (50), which contain rollers (54), are mounted to swivel so the floss span can move in any direction. Thus, the span can wrap around a tooth and reciprocate laterally and vertically thereabout.

11 Claims, 2 Drawing Sheets

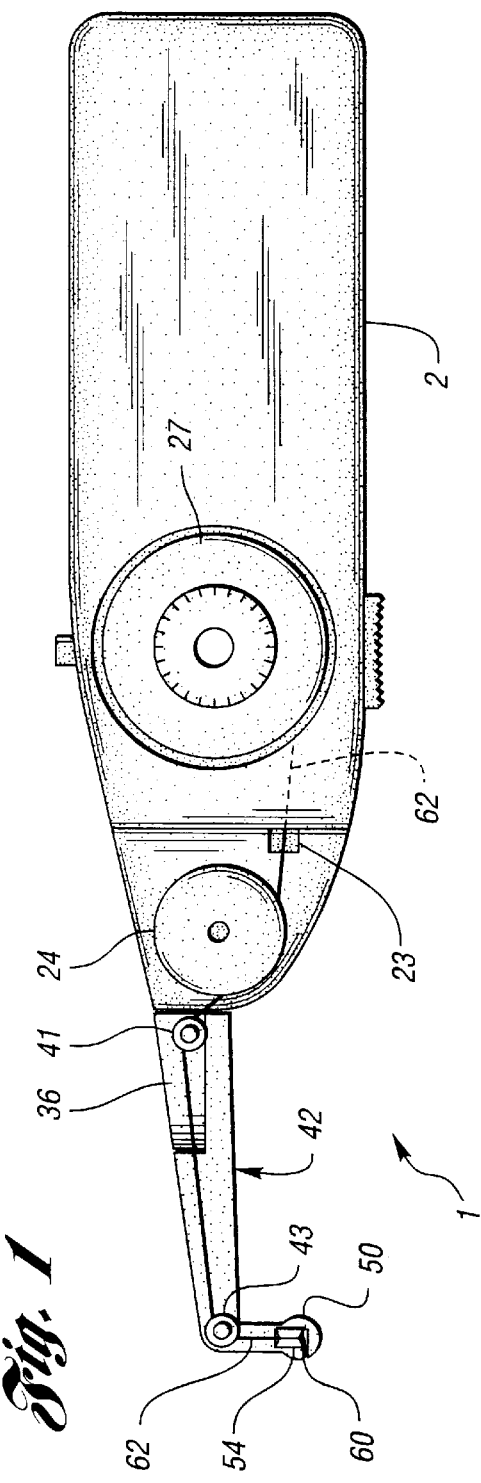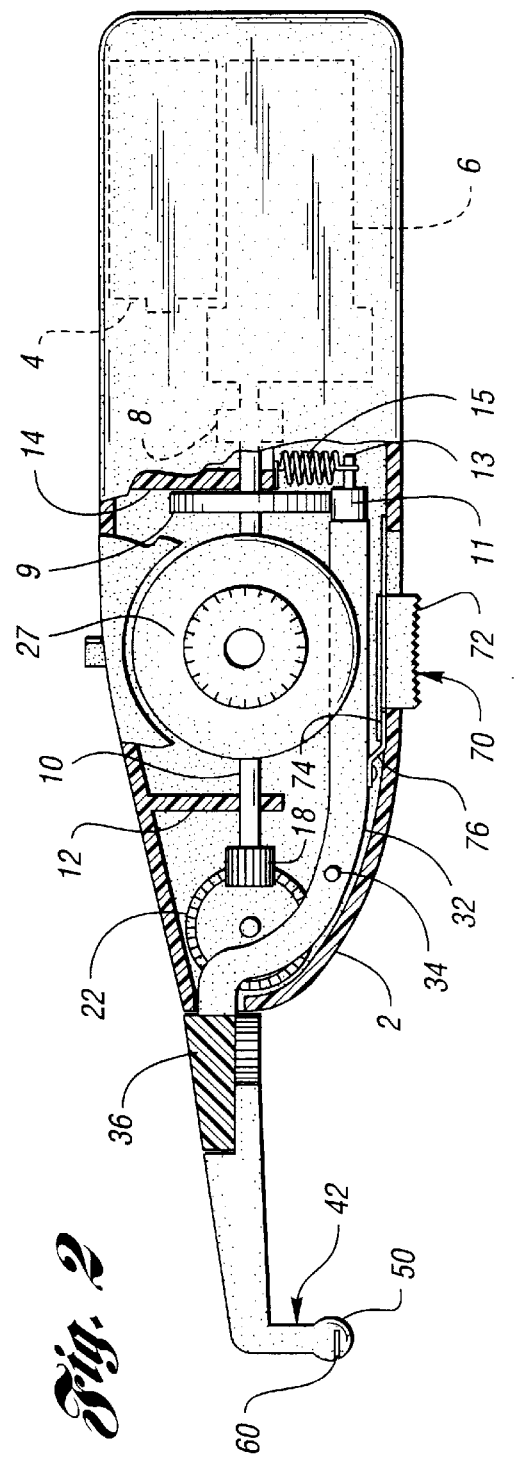

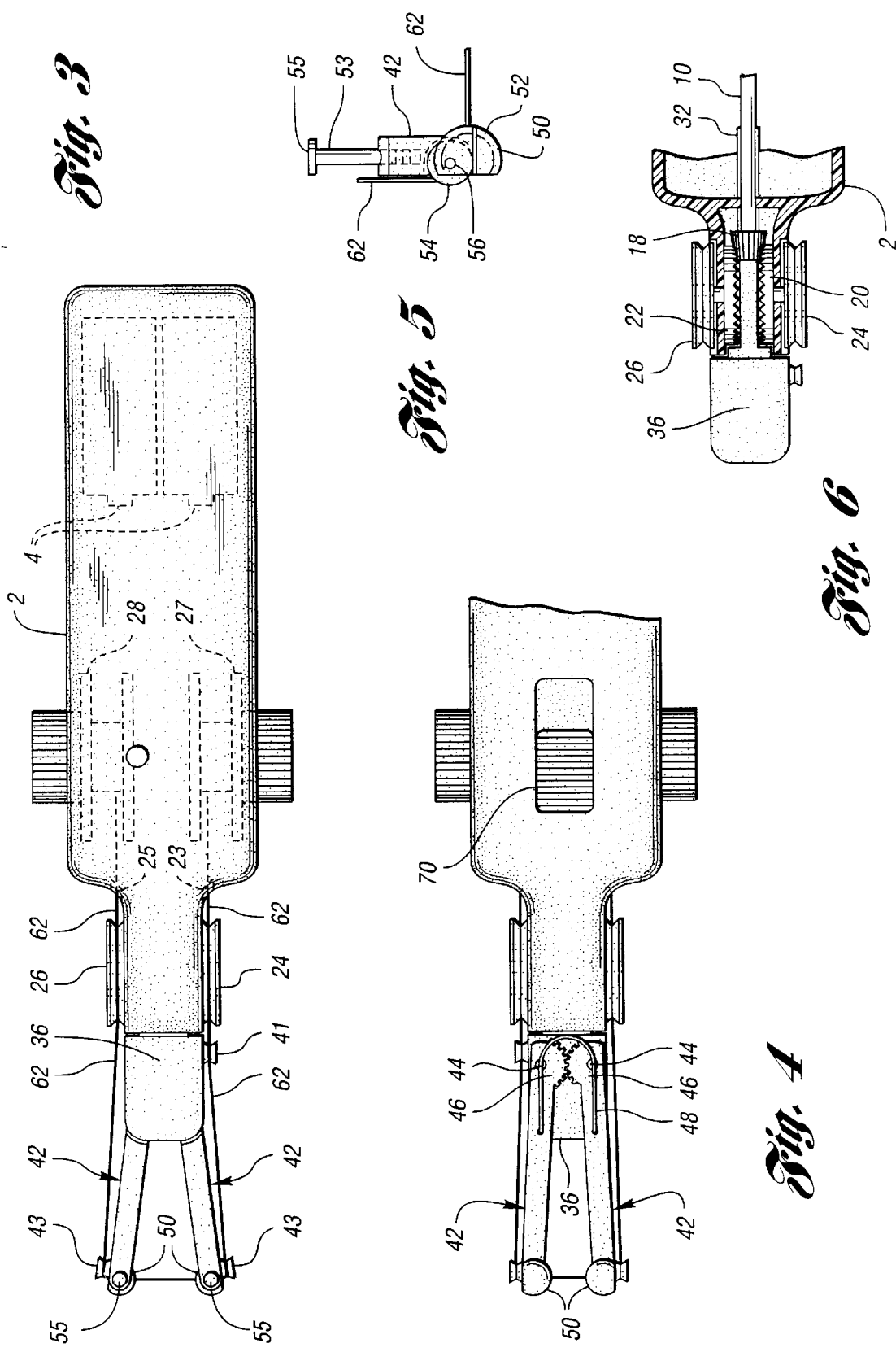

SELF-GUIDING FLOSSER

TECHNICAL FIELD

This invention relates to dental flossing devices and more particularly to flossing devices having power driven means for reciprocating a floss span.

BACKGROUND

Several powered flossers have been patented. Each of them includes a spaced pair of tines in order to support a floss span for flossing teeth.

A limitation of the prior art is that a user must spend time probing with the floss span before finding the precise location of an interdental space; especially between molars. Time must also be spent trying to align the floss span along a tight interdental space in order to enter. Entering may be difficult as proper positioning and aligning of the floss can be awkward, even with the aid of a mirror. Complicating the problem, the floss can get caught at tight contact points between teeth.

The prior art also lacks sufficient means for wrapping the floss span around a tooth and for reciprocating the span when in the wrap-around condition.

The present invention includes guide means for guiding a floss span into an interdental space as the span approaches the general location of the space. The guide means includes laterally pivoting tines which close in on the target location when the floss span meets resistance. Bulbous ends of the tines, which support the floss span, follow the opposing vertical grooves between teeth to guide the span into and through the interdental space. The bulbous ends of the tines swivel so the floss span can move in any direction, thereby allowing the span to wrap around a tooth and reciprocate laterally and vertically thereat. Other advantages will become apparent from consideration of the drawings and ensuing description.

BRIEF DESCRIPTION OF THE DRAWINGS

The accompanying drawings in combination with the description herewith, illustrate features and advantages of the invention. Like reference numerals in different views refer to the same parts. The drawings are intended to illustrate principles of the invention and are not necessarily to scale and in which drawings:

FIG. 1 is a side view of a self-guiding flosser constructed in accordance with the invention;

FIG. 2 is a cross-sectional view taken vertically along the longitudinal center line of the flosser of FIG. 1;

FIG. 3 is a top view of the flosser of FIG. 1;

FIG. 4 is a partial bottom view of the flosser of FIG. 1;

FIG. 5 is a fragmental view of a tine of the flosser of FIG. 1; and

FIG. 6 is a partial top view, partly in section taken horizontally along the longitudinal axis of the flosser of FIG. 1;

DETAILED DESCRIPTION

An embodiment of a self-guiding flosser 1, is shown in FIGS. 1–6. Included in the device are principles of this inventor's Automated Dental Flosser, disclosed in U.S. Pat. No. 5,323,796 issued Jun. 28, 1994. U.S. Pat. No. 5,323,796 is incorporated by reference herein.

Flosser 1 has a frame or housing 2 which houses rechargable batteries 4 (FIGS. 2 and 3) arranged side-by-side for powering a conventional speed-reduction gearmotor 6. A conventional wiring circuit (not shown) connects the batteries to the gearmotor.

A coupling 8 (FIG. 2) drivingly connects the gearmotor to a drive shaft 10 which is rotatably supported by bearing supports 12, 14. A front end portion of the drive shaft is coaxially fixed to a sector gear 18 (FIGS. 2 and 6) which alternately engages a first crown gear 20 (FIG. 6) and a second crown gear 22 when the sector gear is driven. Hence the crown gears are driven alternately and are driven in opposite directions.

First crown gear 20 is fixedly connected coaxially to a first subcapstan 24 by a short shaft. The short shaft is rotatably supported in an aperture though a wall of a narrow front end portion of housing 2. Similarly, the second crown gear 22 is fixedly connected coaxially to a second subcapstan 26 by a second short shaft. The second shaft is rotatably supported in an aperture though an opposite wall of the narrow front portion of housing 2 such that the crown gears and subcapstans rotate about a common axis. As arranged, the gears rotate inside the housing and the subcapstans rotate outside the housing. Thus, subcapstans 24, 26 are driven alternately and are driven in opposite directions.

Each subcapstan 24, 26 includes a rim having an endless grooved portion for engaging floss. The diameter of the grooved portion of the second subcapstan 26 being slightly greater than that of the first subcapstan 24. Hence there is a net floss advance when the second subcapstan is driven.

A floss dispensing spool 27 (FIGS. 1, 2 and 3) and a floss take-up spool 28 are supported, driven, and function in the same manner as the spools of Automated Flosser. Accordingly, drive shaft 10 drives the take-up spool 28 in a like manner as a corresponding drive shaft, in Automated Flosser, drives a take-up spool.

Housing 2 includes slots 23, 25 (FIGS. 1 and 3) to allow floss 62 to extend from the dispensing spool to subcapstan 24 and from subcapstan 26 to the take-up spool (FIG. 3). Thus, the spools and subcapstans interact in a like manner as in Automated Flosser.

A curved lever 32 (FIG. 2) is pivotally mounted within housing 2 and pivots about a pin 34 received in aligned apertures through the lever and housing. A front or anterior end portion of the lever passes through an opening in an anterior end of housing 2.

A pivot base 36 is fixed to the anterior end portion of lever 32. The lever and pivot base are molded as a one-piece unit.

A multi-lobed cam 9 (FIG. 2), similar to the cam of Automated Flosser, is fixed to a posterior portion of drive shaft 10 and engages a cam follower 11. The cam follower comprises a rotor rotatably supported on a pin 13 inserted into a posterior end portion of lever 32.

Attached to pin 13 is one end of a tensioned spring 15. The opposite end of the spring is supported on a small hook attached to support 14 so that pivot base 36 is urged downward by the spring. When the gearmotor drives cam 9 to rotate, each lobe of the cam moves the posterior end of lever 32 downward, thus moving base 36 upward. After each cam lobe passes over the follower, spring 15 returns the base downward. Hence, the base reciprocates up and down as the cam rotates.

A pair of tines 42 are pivotally mounted to an underside of pivot base 36 such that the tines can pivot toward and away from each other. The tines move horizontally between a closed position (FIG. 4) and an open position (FIG. 3).

A posterior end portion of each tine is formed as a sector gear 46 (FIG. 4). The tines are mounted such that each tine sector gear engages the other and each gear pivots about a respective pin 44. Thus, the tines are connected by the gears such that movement of one tine causes symmetrical movement of the other tine.

Connected to the tines is U-shaped spring 48 having each of two end portions bent at a right angle and press fitted into a pin hole in each tine, respectively. When the tines move to the closed position, the spring is stressed and thereby urges the tines to move away from each other to spread apart toward the open position. When the floss-loaded flosser 1 is not flossing, the force of spring 48 keeps the tines in the open position. When flossing, however, increased floss tension from tooth resistance overcomes the spring force to close the tines toward the teeth being flossed.

In addition to moving horizontally between the open and closed positions, the tines also move vertically by reciprocating up and down along with base 36 when the base reciprocates.

As indicated in FIGS. 1 and 2, each tine 42 is L-shaped such that the long leg of the L is approximately horizontal and the short leg is vertical during normal operation of the flosser. A distal end portion of the short leg includes a bulb 50 shaped like a truncated sphere or dome which faces the dome of the other tine. Each bulb includes a coating of rubber or soft plastic 52 (FIG. 5) to form a resilient yielding surface to soften contact with teeth. The height of a short leg of a tine, as measured from the long leg to the center of the bulb, is a bit greater than the height of user's teeth above the gums.

A lower portion of each short leg is pivotally attached to an upper portion by a swivel pin 53 (FIG. 5) so that each bulb can swivel about a vertical axis. A threaded portion of the pin is fixedly screwed into the short leg lower portion. An upper portion of the pin is pivotally received in a vertical bore in the upper portion of the short leg. Pin 53 includes a head 55 (FIGS. 3 and 5) which swivels within an annular recess in the tine and holds the short leg assembly together.

To reduce friction as floss reciprocates and advances through the flosser, the floss is supported on rollers along its route. In the following description, each roller is named according to its location.

A base roller 41 (FIGS. 1 and 3) is rotatably mounted on a lateral side of pivot base 36, adjacent subcapstan 24. A pin, passing through the base roller and inserted into the pivot base, supports the roller.

An elbow roller 43 is rotatably supported on each elbow of each tine. Each elbow roller is supported by a respective pin passing through the roller and inserted into the associated tine elbow.

Each bulb includes a cavity having an entrance on a flat back side of the bulb. The cavity extends into the bulb and receives a bulb roller 54 (FIGS. 1 and 5). The roller is rotatably supported on a pin 56 passing through the bulb. A bottom portion of the roller is positioned along a horizontal midline of the bulb.

A portion of each bulb includes a horizontal opening or slot 60 (FIG. 1) which extends to the rim of the roller. The slot allows floss to be loaded onto the bulb roller and to span across to the opposite bulb.

Floss is routed through the flosser beginning from the dispensing spool 27 and extends onto and around the grooved rim of subcapstan 24 and then onto base roller 41. From roller 41, the floss extends onto elbow roller 43 and then down onto bulb roller 54. From roller 54 the floss spans over to the opposite tine onto its bulb roller, then up onto its elbow roller, and then onto and around subcapstan 26. From subcapstan 26 the floss extends to the take-up spool.

As arranged, floss is movably supported on the bulb rollers to form a floss span extending from the bulb of one tine to the bulb of the other tine. The span can be reciprocated longitudinally of the span (side to side) by the actions of the subcapstans and vertically by the actions the cam 9 and spring 15.

Before entering between teeth, it may be desirable to stop the up and down reciprocating motion of the floss in order to make the entry easier. The side to side reciprocating motion should continue as it will help the span work its way through the tight spot where top portions of teeth come in contact. Once entered, the up and down motion can be resumed.

Therefore, to stop the up and down motion momentarily, a slide switch 70 (FIG. 2) is provided. The switch includes conventional means for allowing the switch button 72 to slide forward and back within a rectangular slot through housing 2. A catch 74 is fixed to an inner side of the switch button and a hook 76 is fixed to lever 32. The catch and hook are angled and aligned such that by sliding the switch button forward (anteriorly), the angled catch engages and slides over the angled hook thereby drawing the lever 32 slightly downward; enough to disengage the cam follower from the cam. Hence, the up and down floss motion stops but side to side motion continues.

When attempting to enter the space between teeth, resistance of a tooth against the floss span causes floss tension to increase. Increased floss tension overcomes the force of spring 48 (which normally keeps the tines apart) so the tines close toward the teeth. The bulbs 50 tend to slide into and follow the vertical grooves between adjacent teeth, thereby guiding and aligning the floss span precisely between teeth to make the entry easy. Hence, the bulbs serve to guide the floss span into interdental spaces so that the user need not spend a lot of time probing to find the spaces.

If resistance is encountered by the floss span, due to a tight spot between teeth, the increased floss tension closes the tines which brace against the teeth. The floss will drawn through the resisting tight spot at the maximum pulling force of the subcapstans.

After passing through the tight spot, the up and down and side to side floss motions can be used. The floss span can be pushed forward or rearward to wrap part-way around a tooth as the span reciprocates. The bulbs swivel to the direction of the extending floss span which becomes U-shaped as it wraps around a tooth. Increased floss tension causes the tines to close on and embrace the tooth while in the warp-around condition. As the floss span reciprocates horizontally (longitudinally) and vertically (up and down), the tines open and close in conformance with the shape of the tooth. Hence, large surface areas around a tooth can be flossed and polished.

While the above description contains many specificities, these should not be construed as limitations on the scope of the invention, but rather as an exemplifications of preferred embodiments. Those skilled in the art will envision other possible variations that are within its scope. Accordingly, the scope of the invention should be determined not by the embodiments illustrated, but by the appended claims and their legal equivalents.

What is claimed is:

1. A flosser comprising:

a frame;

a pair of tines mounted on the frame for supporting a floss span between the tines, at least one of the tines being pivotally supported to be movable toward and away from the other tine, each of the pair of tines having a distal end portion which includes a bulb having an opening and a rotatably supported roller disposed in the opening for movably supporting the floss;

a spring connected to the tines having a spring bias for biasing the tines apart; and floss take-up means for taking up floss from the floss span thereby creating floss tension which overcomes the spring bias and urges the tines toward each other.

2. The flosser as defined in claim 1, wherein each bulb has a resilient yielding surface to soften contact with teeth.

3. A flosser comprising:

a frame;

a pair of tines mounted on the frame for supporting a floss span between the tines, the tines being movably supported to move toward and away from each other; and two gears pivotally mounted and engaged with each other, each gear being attached to a respective tine, the two gears for connecting the tines such that movement of one tine causes approximately symmetrical movement of the other tine.

4. The flosser as defined in claim 3, further comprising a spring connected for urging the tines to move away from each other.

5. A flosser comprising:

a frame; and a pair of spaced tines mounted on the frame, each tine including a distal end portion having a floss supporting portion for supporting a floss span between the tines, the floss supporting portion being mounted to swivel in order to adjust for floss span direction changes.

6. The flosser as defined in claim 5, wherein each tine distal end portion has a bulb which includes an opening for passage of floss therethrough such that the floss span extends from one bulb to the other bulb, each bulb having a resilient yielding surface to soften contact with teeth.

7. The flosser as defined in claim 5, wherein each tine distal end portion has a bulb which includes a cavity and a rotatably supported roller within the cavity, each bulb having an opening for passage of floss therethrough such that the floss span extends from one bulb to the other bulb and the floss is movably supported on the bulb rollers.

8. A flossing device for flossing a user's teeth with dental floss, the flossing device comprising:

a frame;

a motor mounted to the frame;

a pair of tines mounted on the frame for supporting a span of dental floss between the tines, at least one of the tines being movable toward and away from the other tine;

a floss dispensing spool rotatably affixed to the frame for providing dental floss to the span;

a floss take-up spool rotatably affixed to the frame for taking dental floss from the span; and a drive mechanism mounted to the motor and driving the floss dispensing spool and floss take-up spool for reciprocating the span of dental floss between the tines in a first direction aligned with the span, while automatically incrementally advancing dental floss from the floss dispensing spool to the floss take-up spool, the drive mechanism causing the pair of tines to move in a second direction orthogonal to the first direction relative to the housing.

9. The flossing device of claim 8, wherein the drive mechanism includes a pair of capstans which are alternately driven in opposite directions causing the dental floss to reciprocate.

10. The flossing device of claim 9, wherein each of the pair of capstans has a groove for engaging dental floss, one of the grooves having a diameter slightly greater than the other causing the dental floss to incrementally advance from the floss dispensing spool to the floss take-up spool.

11. The flossing device of claim 8, further comprising a spring connected for urging the tines to spread apart.

\* \* \* \* \*